(12) United States Patent
Doppiu et al.

(10) Patent No.: US 8,716,509 B2
(45) Date of Patent: May 6, 2014

(54) PROCESS FOR PREPARING RUTHENIUM(0)-OLEFIN COMPLEXES

(75) Inventors: Angelino Doppiu, Seligenstadt (DE); Andreas Rivas-Nass, Schriesheim (DE); Ralf Karch, Kleinostheim (DE); Roland Winde, Frankfurt (DE); Eileen Woerner, Nidderau (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 20 days.

(21) Appl. No.: 13/505,796

(22) PCT Filed: Nov. 11, 2010

(86) PCT No.: PCT/EP2010/006858
§ 371 (c)(1),
(2), (4) Date: Jul. 10, 2012

(87) PCT Pub. No.: WO2011/057780
PCT Pub. Date: May 19, 2011

(65) Prior Publication Data
US 2012/0277456 A1    Nov. 1, 2012

(30) Foreign Application Priority Data
Nov. 14, 2009   (DE) .................. 10 2009 053 392

(51) Int. Cl.
*C07F 15/00*   (2006.01)
*C23C 16/00*   (2006.01)

(52) U.S. Cl.
USPC .............. 556/136; 427/252; 427/255.19

(58) Field of Classification Search
USPC .............. 556/136; 427/252, 255.19
See application file for complete search history.

(56) References Cited

U.S. PATENT DOCUMENTS

2009/0238970 A1   9/2009  Taniuchi

FOREIGN PATENT DOCUMENTS

EP    1 604 964 A1   12/2005

OTHER PUBLICATIONS

Allardyce et al., Platinum Metals Rev., vol. 45, No. 2, pp. 62-69 (2001).*
Yan et al., Chemical Communications, Issue 38, pp. 4764-4776 (2005).*
International Search Report for PCT/EP2010/006858, dated Jul. 1, 2011.
Written Opinion of the International Searching Authority for PCT/EP2010/006858, dated Jul. 1, 2011.
Bauer, A., et al.: "Efficient synthesis of ruthenium(II) eta-5-dienyl compounds starting from di-mu-chlorodichlorobis [(1-3eta:6-8eta)-2,7-dimethyloctadienediyl]diruthenium(IV). Versatile precursors for enantioselective hydrogenation catalysts", Organometallics, 2000, pp. 5471-5476, XP002616974.
Pertici, P., et al.: "A new synthetic method for the preparation of cyclo-olefin ruthenium complexes", J. Chem. Soc., Dalton Transactions, 1980, pp. 1961-1964, XP002616975.

* cited by examiner

*Primary Examiner* — Porfirio Nazario Gonzalez
(74) *Attorney, Agent, or Firm* — Levine Santalone LLP; John Santalone

(57) ABSTRACT

The present invention relates to a process for preparing ruthenium(0)-olefin complexes of the (arene)(diene)Ru(0) type by reacting a ruthenium starting compound of the formula Ru(+II)$(X)_p(Y)_q$ (in which X=an anionic group, Y=an uncharged two-electron donor ligand, p=1 or 2, q=an integer from 1 to 6), with a cyclohexadiene derivative or a diene mixture comprising a cyclohexadiene derivative, in the presence of a base. In this process, the arene bound in the (arene)(diene)Ru(0) complex is formed from this cyclohexadiene derivative by oxidation. Suitable ruthenium(II) starting compounds are, for example, $RuCl_2$(acetonitrile)$_4$, $RuCl_2$(pyridine)$_4$ or $RuCl_2$(DMSO)$_4$. The bases used are inorganic or organic bases. The ruthenium(0)-olefin complexes prepared by the process according to the invention have a high purity and can be used as precursors for homogeneous catalysts, for preparation of functional ruthenium- or ruthenium oxide-containing layers and for therapeutic applications.

24 Claims, No Drawings

PROCESS FOR PREPARING RUTHENIUM(0)-OLEFIN COMPLEXES

BACKGROUND OF THE INVENTION

The present invention relates to a process for preparing ruthenium(0)-olefin complexes of the (arene)(diene)Ru(0) type. These complexes are organometallic ruthenium compounds in which the central ruthenium atom has the +−0 oxidation state and is bound in the manner of a sandwich between two olefinic ligands. In these complexes, the arene group provides three double bonds and the diene group two double bonds, each in π-bonded coordination, to the central Ru(0) atom.

In the process according to the invention, an Ru(II) starting compound of the formula $Ru(II)X_p(Y)_q$ is reacted in the presence of a base with a suitable cyclohexadiene derivative, which acts as a reducing agent, is oxidized to the arene ligand and is coordinated in this form to the central atom which has been reduced to Ru(0). The corresponding Ru(0)-olefin compounds are obtained in high purity and good yield.

Ruthenium(0) complexes are gaining increasing significance as starting materials for preparation of homogeneous catalysts. The compounds also find use as precursors for obtaining functional coatings with the aid of thin-layer processes, for example MO-CVD (metal-organic chemical vapour deposition), PVD (physical vapour deposition) or ALD (atomic layer deposition). Ru(0) complexes can also have therapeutic effects and find uses in medicine, for example as cytostatics.

The literature discloses various processes for preparing ruthenium(0)-olefin complexes. Most of these compounds additionally contain CO ligands. The frequently used complexes of this class, for example $(1,3\text{-cyclohexadiene})Ru(CO)_3$ or $(1,5\text{-cyclooctadiene})Ru(CO)_3$, are prepared by reacting trisruthenium dodecacarbonyl $(Ru_3(CO)_{12})$ with the corresponding diene (on this subject, cf., for example U.S. Pat. No. 7,238,822).

WO 2008/078296A1 discloses Ru(0) complexes which contain an arene group and a diene group. They are used to prepare Ru or $RuO_2$ films by means of CVD or ALD. The Ru(0) complexes are prepared in a two-stage process, in which a cyclohexadiene ligand is first reacted with Ru(III) chloride in an alcohol. This forms the dimeric complex $[(\text{arene})Ru(II)Cl_2]_2$. This dimeric intermediate is converted by addition of a further diene ligand to the compound of the (arene)(diene)Ru(0) type. The disadvantage here is that the process is performed in two stages and, in the second stage, a diene excess is used, which leads to contaminated products. Moreover, the yields are reduced by the multistage process.

US 2009/0238970 A1 describes Ru(0) complexes of the (arene)(norbornadiene)Ru(0) type, which contain norbornadiene as the diene. The Ru(0) complexes are likewise prepared in a two-stage process via the dimeric complex $[(\text{arene})Ru(II)Cl_2]_2$. The dimeric intermediate is converted by addition of norbornadiene in excess and of a base to a compound of the (arene)(norbornadiene)Ru(0) type. Here too, the process has two stages and is afflicted with the disadvantages already mentioned.

EP 1,604,964B1 describes a process for preparing Ru(0) complexes of the (arene)(diene)Ru(0) type, in which the dimeric starting compound $[(\text{arene})Ru(II)Cl_2]_2$ is reacted with a corresponding diene ligand under reducing conditions. The crude product is purified and isolated by hot extraction with a saturated hydrocarbon solvent. The process again has two stages and generally has to be carried out under inert and anhydrous conditions.

A. Salzer et al. (*Organometallics* 2000, 19, p. 5471-5476) describe a process for preparing $(\eta^6\text{-benzene})(\eta^4\text{-1,3-cyclohexadiene})$ruthenium(0), in which the dichloro(2,7-dimethylocta-2,6-diene-1,8-diyl)ruthenium(IV) starting compound is reacted with cyclohexadiene in excess. The process has the disadvantage that the Ru(IV) starting compound has to be prepared in a complex process. In the event that the reduction does not proceed quantitatively, residues of Ru(III) or Ru(IV) and polymeric components may remain. As a result, the process is costly overall and barely suitable for industrial use.

P. Pertici and G. Vitulli (*J.C.S. Dalton Trans.*, 1980, p. 1961-1964) describe a process for preparing cyclic ruthenium-olefin complexes, especially of $(\eta^6\text{-benzene})(\eta^4\text{-1,3-cyclohexadiene})$ruthenium(0) and $(\eta^6\text{-cyclooctatriene})(\eta^4\text{-1,5-cyclooctadiene})$ruthenium(0), in which the ruthenium (III) trichloride hydrate starting compound is reacted with a large (generally 30- to 50-fold) excess of corresponding diene ligand in the presence of excess zinc dust as a reducing agent. This results in a disproportionation reaction of the diene used to form the corresponding triene and the monoene. As a result of this, and owing to the high olefin excess, the product is additionally contaminated by polymeric and oligomeric substances. In addition, residues of zinc may remain and contaminate the product.

It was therefore an object of the present invention to provide a process for preparing ruthenium(0)-olefin complexes which provides products in high purity and high yield and is suitable for economic industrial application. The process should also have one stage and be based on starting compounds preparable in a simple manner.

SUMMARY OF THE INVENTION

The present invention relates to a process for preparing ruthenium(0)-olefin complexes of the (arene)(diene)Ru(0) type by reacting a ruthenium starting compound of the formula

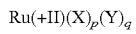

$$Ru(+II)(X)_p(Y)_q$$

in which
X=an anionic group,
Y=an uncharged two-electron donor ligand,
p=1 or 2,
q=an integer from 1 to 6,
with a cyclohexadiene derivative or a diene mixture comprising a cyclohexadiene derivative, in the presence of a base, wherein the arene bound in the ruthenium(0)-olefin complex is formed from this cyclohexadiene derivative by oxidation.

The cyclohexadiene derivative (or the diene mixture comprising a cyclohexadiene derivative) is reacted with the ruthenium(II) starting compound $Ru(+II)(X)_p(Y)_q$ in the presence of an inorganic and/or organic base. The central ruthenium atom of the starting compound is reduced by the cyclohexadiene derivative from Ru(II) to Ru(0), and is oxidized to form an aromatic triene (an "arene" or benzene system).

DETAILED DESCRIPTION OF THE INVENTION

The process according to the invention can in principle be performed in two variants. The first variant comprises the use of a cyclohexadiene derivative without an additional diene. In this case, this cyclohexadiene derivative and the aromatic triene (=arene) formed by oxidation therefrom are coordinated onto the reduced Ru(0). In this case, the cyclohexadiene derivative thus functions both as a reducing agent and as a diene ligand for the reduced Ru(0). This gives (arene)(diene)Ru(0) complexes which have, as well as a six-membered aromatic system, a cyclohexadiene derivative. For this purpose, at least 2 mol of the cyclohexadiene derivative (based on the Ru of the starting compound) have to be used.

The second variant of the process according to the invention comprises the use of a diene mixture which comprises a cyclohexadiene derivative. In this case, the arene formed by oxidation is bonded to the central Ru(0) atom together with the diene present in the mixture. The cyclohexadiene derivative functions here as a reducing agent; as well as the arene formed therefrom, the further diene present in the mixture is bonded as a ligand to the reduced Ru(0). This gives mixed (arene)(diene)Ru(0) complexes. For this purpose, at least 1 mol of the cyclohexadiene derivative and at least 1 mol of the additional diene (based in each case on the Ru of the starting compound) have to be used.

In both variants, the diene is bonded to the central Ru(0) atom in the form of a 4-electron π-bond, and the arene in the form of a 6-electron π-bond. This gives sandwich-type ($\eta^6$-arene)($\eta^4$-diene)Ru(0) complexes which have a stable 18-electron configuration.

Combinations or mixtures of different dienes are useable in the process according to the invention when at least one of the dienes used is a substituted or unsubstituted cyclohexadiene derivative and can bring about the reduction of the central atom of the starting compound from Ru(II) to Ru(0). The arene derivative formed by oxidation from this cyclohexadiene derivative is bound within the ruthenium(0)-olefin complex. As a further ligand, the diene present in the mixture coordinates to the Ru(0). For a selected diene (1,3-cyclohexadiene here) and the starting compound Ru(+II)Cl$_2$(acetonitrile)$_4$, the reaction principle of the present invention can be represented illustratively as follows:

(1) Oxidation

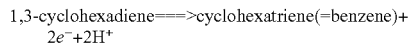

(2) Reduction

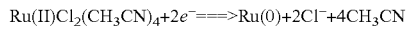

(3) Overall Reaction (1)+(2)

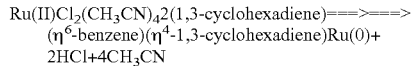

The role of the base used consists in neutralizing the acid released in the reaction (HCl in this case).

In the process according to the invention, a ruthenium starting compound of the formula Ru(+II)(X)$_p$(Y)$_q$ is used, in which the Ru is present in the +II oxidation state, X is an anionic group, Y is an uncharged two-electron donor ligand, p is either 1 or 2 and q is an integer from 1 to 6.

The uncharged two-electron donor ligands Y used are ligands which can be coordinated to the ruthenium. Suitable two-electron donor ligands Y are selected from the group of acetonitrile, benzonitrile, acrylonitrile, methylisonitrile (CNCH$_3$), water, THF, dioxane, dimethyl sulphoxide (DMSO), dimethylformamide (DMF), acetone, ammonia (NH$_3$), amines and pyridine. In a preferred embodiment, the ligands Y are solvent molecules or solvent ligands and are selected from the group of acetonitrile, benzonitrile, water, THF, dioxane, dimethyl sulphoxide (DMSO), dimethylformamide (DMF), acetone and pyridine.

The ruthenium starting compound may also have mixtures and combinations of these different two-electron donor ligands Y.

For the inventive reaction, simultaneous coordination of the diene and of the arene formed in the reaction to the central Ru(II) atom is important. This is enabled by the easy exchange of the uncharged two-electron donor ligands Y for the arene or diene ligands. The desired ($\eta^6$-arene)($\eta^4$-diene)Ru(0) complexes are thus obtained in high purity and very good yield.

Examples of the anionic X group in the ruthenium starting compound are monoanions such as halides (e.g. F$^-$, Cl$^-$, Br$^-$ or I$^-$), pseudohalides (e.g. CN$^-$, CNO$^-$ or SCN$^-$), acetylacetonates, tosylates (CH$_3$C$_6$H$_4$SO$_3^-$), trifluoromethylsulphonates ("triflate"; CF$_3$SO$_3^-$), and also acetates or trifluoroacetates. When monoanions are used, p=2. The anionic X group may, however, also include dianions, for example sulphates (SO$_4^{2-}$), hydrogenphosphates (HPO$_4^{2-}$), oxalates (C$_2$O$_4^{2-}$) and carbonates (CO$_3^{2-}$). In this case, p=1.

Examples of suitable starting compounds of the Ru(+II) (X)$_p$(Y)$_q$ type are RuCl$_2$(acetonitrile)$_4$, RuBr$_2$(acetonitrile)$_4$, RuCl$_2$(pyridine)$_4$, [Ru(H$_2$O)$_6$]Cl$_2$, [Ru(H$_2$O)$_6$](tosylate)$_2$, [Ru(H$_2$O)$_2$](acetate)$_2$, RuCl$_2$(DMSO)$_4$, [Ru(NH$_3$)$_6$]Cl$_2$, RuCl$_2$(benzonitrile)$_4$. Such compounds are known to those skilled in the art and are preparable by literature methods (cf., for example, W. E. Newton and J. E. Searles, *Inorganica Chimica Acta*, 1973, 3, p. 349-352 or F. M. Lever, A. R. Powell, *J. Chem. Soc.* (A), 1969, p. 1477-1482).

In the process of the present invention, cyclohexadiene derivatives or diene mixtures comprising a cyclohexadiene derivative are used. The cyclohexadiene derivative may be an unsubstituted cyclohexadiene derivative, a mono-alkyl-substituted cyclohexadiene derivative, a poly-alkyl-substituted cyclohexadiene derivative, or a mixture thereof.

Examples of unsubstituted cyclohexadienes are 1,3-cyclohexadiene and 1,4-cyclohexadiene, or mixtures thereof.

Examples of mono-alkyl-substituted cyclohexadienes are 1-methyl-1,3-cyclohexadiene, 1-methyl-1,4-cyclohexadiene, 1-ethyl-1,3-cyclohexadiene, 1-ethyl-1,4-cyclohexadiene.

Examples of poly-alkyl-substituted cyclohexadienes are 1-isopropyl-4-methyl-1,3-cyclohexadiene (α-terpinene), 1-isopropyl-4-methyl-1,4-cyclohexadiene (γ-terpinene) and 2-methyl-5-isopropyl-1,3-cyclohexadiene (α-phellandrene) or bicyclo-[4.3.0]-nona-3,6(1)-diene or mixtures thereof.

In addition, it is possible to use further substituted cyclohexadiene derivatives; permissible substituents include, each independently, aryl groups, halogens, acyl groups, alkoxy groups, alkoxycarbonyl groups, silyl groups, siloxane groups, and mixtures and combinations thereof.

Combinations or mixtures of different dienes are useable efficiently in the process according to the invention, as already described. They lead to the preparation of mixed (arene)(diene)Ru(0) complexes. In this second variant of the process already described, a diene mixture is used, which, as well as an unsubstituted or substituted cyclohexadiene derivative, additionally comprises a substituted or unsubstituted, cyclic or noncyclic diene (on this subject, cf. Example 8).

Examples of suitable cyclic dienes are 1,3-cyclooctadiene, 1,5-cyclooctadiene, norbornadiene, dicyclopentadiene and spiro[2.4]hepta-4,6-diene or mixtures thereof.

Examples of noncyclic dienes are butadiene, isoprene, 2,3-dimethyl-1,3-butadiene, 1,3-pentadiene, 1,4-pentadiene and 2,4-dimethyl-1,3-pentadiene, and mixtures thereof.

In addition, it is possible to use further substituted diene derivatives or diene analogs; further permissible substituents include, each independently, aryl groups, halogens, acyl groups, alkoxy groups, alkoxycarbonyl groups, silyl groups, siloxane groups, and mixtures and combinations thereof. Diene analogs are understood here to mean compounds which have at least two C=C double bonds which need not be conjugated. Examples of suitable diene analogs are 1,3-divinyltetramethyldisiloxane ("VTS") or 1,3-divinyltetramethyldisilazane. The diene analog provides two double bonds, in each case in π-bonded coordination, to the central Ru(0) atom.

When substituted or unsubstituted 1,4-cyclohexadiene derivatives are used, they are generally converted during the inventive reaction to the 1,3-cyclohexadiene systems which are more stable, since they are conjugated, and are bonded in this form to the Ru(0) (on this subject, cf. Examples 9, 10 and 11).

The reaction of 1-isopropyl-4-methyl-1,3-cyclohexadiene (α-terpinene), 1-isopropyl-4-methyl-1,4-cyclohexadiene (γ-terpinene) or 2-methyl-5-isopropyl-1,3-cyclohexadiene (α-phellandrene) with the Ru starting compound of the Ru(+II)(X)$_p$(Y)$_q$ type to give (η$^6$-p-cymene)(η$^4$-1-isopropyl-4-methylcyclohexadiene)ruthenium(0) surprisingly forms, in all cases, an isomer mixture of three structural isomers, each of which has a 1,3-conjugated double bond system and to which the following structural formulae can be assigned:

Isomer A

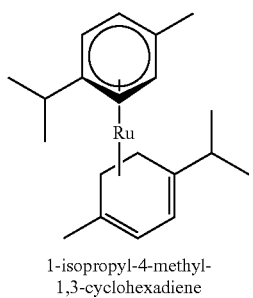

1-isopropyl-4-methyl-
1,3-cyclohexadiene

Isomer B

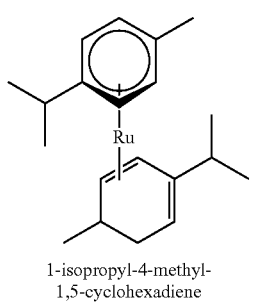

1-isopropyl-4-methyl-
1,5-cyclohexadiene

Isomer C

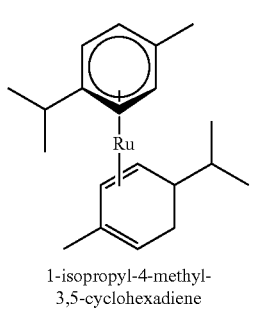

1-isopropyl-4-methyl-
3,5-cyclohexadiene

This compound is obtained as an isomer mixture wherein at least two of the isomers are present in a ratio of 1:5 to 5:1, preferably 1:2 to 2:1. The compound thus obtained is in liquid form at room temperature (20° C.) and has advantages in application, for example in metered addition in CVD and ALD processes).

The typical amounts added for the diene or the diene mixture are 2 to 5 equivalents, preferably 2 to 4 equivalents and more preferably 2 to 3 equivalents, based in each case on the ruthenium starting complex. In the case of use of two different dienes, the total amount added is divided in a suitable ratio, in which case the addition can be effected in parallel or successively.

The bases used are inorganic and/or organic bases. Examples of inorganic bases are alkali metal or alkaline earth metal hydroxides such as NaOH, KOH or Ca(OH)$_2$, alkali metal or alkaline earth metal carbonates such as lithium carbonate (Li$_2$CO$_3$), sodium carbonate (Na$_2$CO$_3$), sodium hydrogencarbonate (NaHCO$_3$) or calcium carbonate (CaCO$_3$), alkali metal or alkaline earth metal phosphates such as Na$_3$PO$_4$, alkali metal or alkaline earth metal oxalates such as sodium oxalate (Na$_2$C$_2$O$_4$), alkali metal or alkaline earth metal acetates such as sodium acetate (CH$_3$COONa), alkali metal or alkaline earth metal acetylacetonates such as sodium acetylacetonate (CH$_3$COCHCOCH$_3$Na), and basic oxides such as calcium oxide (CaO) or aluminium oxide (Al$_2$O$_3$). Examples of organic bases are ammonia, diethylamine, trimethylamine, triethylamine, urotropin, ethanolamine, pyridine, triethanolamine, DBU (1,8-diazabicyclo-[5.4.0]-undec-7-ene), DBN (diazabicyclononane), DABCO (1,4-diazabicyclo-[2.2.2]-octane), imidazole or ethylenediamine. Other bases, especially organometallic bases which have a carbanion (for example n-butyllithium, methyllithium, tert-butyllithium, sodium cyclopentadienide or Grignard reagents), are not used. Owing to their sensitivity to water, they are unsuitable for the conditions of the process according to the invention.

It is also possible to use mixtures of the organic and inorganic bases mentioned. Preference is given to inorganic bases, especially lithium carbonate (Li$_2$CO$_3$), sodium phosphate (Na$_3$PO$_4$) and sodium carbonate (Na$_2$CO$_3$). The amounts added for the base are 1 to 20 equivalents, preferably 2 to 5 equivalents, based in each case on the Ru starting complex.

The process of the present invention can in principle be performed in all common polar protic or aprotic organic solvents. Advantageously, polar organic solvents from the class of the alcohols, ketones, ethers, amides or esters are used. Examples of suitable polar aprotic organic solvents are acetone, THF, dimethylformamide (DMF), ethylene glycol dimethyl ether, dioxane and mixtures thereof. Examples of suitable polar protic organic solvents are methanol, ethanol, isopropanol, tert-butanol, methoxyethanol, ethylene glycol and mixtures thereof. The organic solvents need not be dried before use. The process according to the invention, in contrast to the prior art, can also be performed in nonalcoholic solvents and in aqueous solvent mixtures (on this subject cf. Examples 3 and 4). The process is preferably performed in a mixture of a polar organic solvent with water (i.e. in an aqueous solvent mixture). Examples of suitable mixtures of polar organic solvents with water are isopropanol/water, ethanol/water, acetone/water, THF/water or dioxane/water, in each case using demineralized, i.e. deionized water. The volume-based mixing ratio of polar organic solvent/demineralized water is in the range from 1:20 to 20:1, preferably in the range from 1:10 to 10:1 and more preferably in the range from 1:5 to 5:1.

The inventive reaction is effected at temperatures between −30 and 120° C., preferably between 20 and 100° C. and more preferably between 30 and 90° C., and the reaction advantageously takes place under reflux.

To perform the process, the Ru(+II) starting compound prepared by literature methods is initially charged in a polar organic solvent or in an aqueous solvent mixture. Then the corresponding diene or the diene mixture and the base are added in portions. The mixture is heated at temperatures in the range between −30 and 120° C., preferably under reflux, for 0.5 to 10 hours, preferably 2 to 5 hours, and then cooled. Subsequently, the product can be extracted with nonpolar organic solvents, for example hexane, pentane, cyclohexane or toluene. After the solvent has been drawn off, the product thus obtained is dried. In an alternative workup step, the product can also be precipitated out of the reaction mixture by adding a polar protic solvent (for example water or ethylene glycol), then removed by filtration and subsequently dried.

In a further preferred embodiment of the process according to the invention, the Ru starting compound of the Ru(+II) (X)$_p$(Y)$_q$ type is prepared in a preceding step ("in situ") and used directly in the process without intermediate isolation (on this subject cf. the "one-pot process" in Example 6). This combines the preparation of the Ru starting compound with the preparation of the (arene)(diene)Ru(0) complex. This variant is particularly time- and cost-saving since simple, readily obtainable ruthenium starting compounds (for example ruthenium(III) chloride hydrate, Ru(III) chloride solution or Ru(III) sulphate solution) are used. The solvent used is a mixture of a polar organic solvent or an aqueous solvent mixture and a small excess of the ligand Y; the reducing agent used is hydrogen/Pt black or hydrazine. For this embodiment of the process, Ru starting compounds with acetonitrile ($CH_3CN$) or DMSO as ligands Y have been found to be the most useful.

It has been found that, surprisingly, the process according to the invention gives the (arene)(diene)Ru(0) complexes in high purity and very good yield. In general, yields in the range between 60 and 95% can be achieved. Owing to the use of Ru(II) starting compounds which contain uncharged two-electron donor or solvent ligands, the ligand exchange by the diene and arene ligands proceeds very gently and virtually quantitatively. Since the process uses water-insensitive, air-stable, inorganic and/or organic bases, it is possible to use environmentally friendly aqueous solvent mixtures. For these reasons, the process according to the invention is particularly suitable for industrial conditions.

After extraction or precipitation, the purity of the (arene)(diene)Ru(0) complexes is more than 90%, preferably more than 95% and more preferably more than 98%. To achieve a higher purity, the product can be subjected to a sublimation or distillation step. Purities of more than 99% can thus be achieved.

The inventive (arene)(diene)Ru(0) complexes find use as starting materials for preparation of homogeneous catalysts. In addition, they are used as precursors for production of functional ruthenium- or ruthenium oxide-containing layers, for example for semiconductor technology (e.g. as an electrode material in CMOS chips or DRAM memory chips). The Ru- or Ru oxide-containing layers are deposited as thin films with the aid of different deposition processes, for example by CVD (chemical vapour deposition), MO-CVD (metal-organic chemical vapour deposition), PVD (physical vapour deposition) or ALD (atomic layer deposition). In the course of this, the (arene)(diene)Ru(0) complexes are decomposed. The inventive complexes also have therapeutic effects and find applications in medicine, for example as cytostatics.

The examples which follow serve for illustration and are intended to describe the invention in detail without restricting the scope of protection thereof.

EXAMPLE 1

Preparation of ($\eta^6$-benzene)($\eta^4$-1,3-cyclohexadiene) ruthenium(0) from 1,3-cyclohexadiene in Isopropanol/Water Formula:

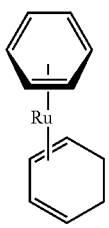

Reaction Equation:

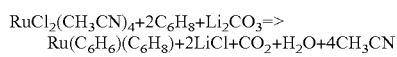

$RuCl_2(CH_3CN)_4$ (from Umicore Hanau, 29.3% by weight of Ru, 5 g, 15 mmol) and $Li_2CO_3$ (4.4 g, 59 mmol) are initially charged in a flask. Isopropanol (100 ml), demineralized water (50 ml) and 1,3-cyclohexadiene (from Aldrich, 5.8 ml, 59 mmol, 4 equivalents) are added. The suspension is brought to reflux (oil bath temperature 90° C.). The light brown-orange mixture is stirred at reflux for four hours and then cooled to room temperature. The reaction mixture is extracted with n-hexane until the extract is colourless. The combined organic phases are washed once with demineralized water, dried over $MgSO_4$ and then filtered. The clear yellow solution is subjected to rotary evaporation, and the resulting crystalline pale yellow product is dried to constant weight under reduced pressure at room temperature.

Yield: 3.2 g, 82%; melting point 112° C.; purity: ≥98% ($^1$H-NMR)

$^1$H NMR ($CD_2Cl_2$), δ (ppm): 1.3 (m, 4H, $CH_2$), 2.9 (m, 2H, CH), 4.6 (m, 2H, CH), 5.2 (s, 6H, CH).

$^1$H NMR ($C_6D_6$), δ (ppm): 1.7 (m, 2H, $CH_2$), 1.8 (m, 2H, $CH_2$), 3.2 (m, 2H, CH), 4.85 (m, 2H, CH), 4.91 (s, 6H, CH).

EXAMPLE 2

Preparation of ($\eta^6$-benzene)($\eta^4$-1,3-cyclohexadiene) ruthenium(0) from 1,4-cyclohexadiene in Ethanol/Water Reaction Equation:

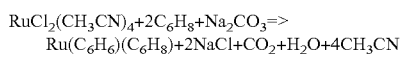

$Ru(II)Cl_2$(acetonitrile)$_4$ (from Umicore, Hanau, 29.3% by weight of Ru, 10 g, 29 mmol) and $Na_2CO_3$ (12.3 g, 0.12 mol) are initially charged in a flask. Ethanol (100 ml), demineralized water (50 ml) and 1,4-cyclohexadiene (from Aldrich, 11.4 ml, 116 mmol, 4 eq.) are added. The suspension is inertized with protective gas and brought to reflux (oil bath temperature 90° C.). The brown mixture is stirred at reflux for 2 hours and then cooled to room temperature. 100 ml of demineralized water are added. The reaction mixture is filtered through a D4 glass frit, then the filtercake is washed with water. The resulting product in the form of yellow needles is dried to constant weight under vacuum at room temperature.

Yield: 6.5 g, 87%. Purity: ≥98% ($^1$H NMR)

$^1$H NMR ($C_6D_6$), δ (ppm): 1.7 (m, 2H, $CH_2$), 1.8 (m, 2H, $CH_2$), 3.2 (m, 2H, CH), 4.85 (m, 2H, CH), 4.91 (s, 6H, CH).

EXAMPLE 3

Preparation of ($\eta^6$-benzene)($\eta^4$-1,3-cyclohexadiene) ruthenium(0) from 1,4-cyclohexadiene in Acetone/Water Reaction Equation: See Example 2

$Ru(II)Cl_2$(acetonitrile)$_4$ (from Umicore, Hanau, 29.3% by weight of Ru, 10 g, 29 mmol) and $Na_2CO_3$ (9.2 g, 0.09 mol) are initially charged in a Schlenk flask. Acetone (100 ml), demineralized water (100 ml) and 1,4-cyclohexadiene (from Aldrich, 10 ml, 0.1 mol, 3.5 eq.) are added. The suspension is inertized with protective gas and brought to reflux (oil bath temperature 90° C.). The brown mixture is stirred at reflux for 2 hours and then cooled to room temperature. 100 ml of demineralized water are added. The reaction mixture is filtered through a D4 glass frit, then the filtercake is washed with water. The resulting product in the form of yellow needles is dried to constant weight under vacuum at room temperature.

Yield: 6.5 g, 87%.

EXAMPLE 4

Preparation of ($\eta^6$-benzene)($\eta^4$-1,3-cyclohexadiene)ruthenium(0) from 1,4-cyclohexadiene in Dioxane/Water Reaction Equation: See Example 2

Ru(II)Cl$_2$(acetonitrile)$_4$ (from Umicore, Hanau, 29.3% by weight of Ru, 10 g, 29 mmol) and Na$_2$CO$_3$ (6.1 g, 0.06 mol) are initially charged in a Schlenk flask. 1,4-Dioxane (60 ml), demineralized water (30 ml) and 1,4-cyclohexadiene (from Aldrich, 8.5 ml, 90 mmol, 3 eq.) are added. The suspension is inertized with protective gas and brought to reflux (oil bath temperature 105° C.). The brown mixture is stirred at reflux for 1 hour and then cooled to room temperature. 100 ml of demineralized water are added. The reaction mixture is filtered through a D4 glass frit. The filtercake is washed with water. The resulting product in the form of yellow needles is dried to constant weight under vacuum at room temperature.

Yield: 5.25 g, 70%.

EXAMPLE 5

Preparation of ($\eta^6$-benzene)($\eta^4$-1,3-cyclohexadiene)ruthenium(0) from 1,4-cyclohexadiene with NEt$_3$ as a Base in Ethanol/Water Reaction Equation:

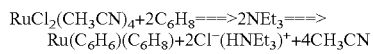

RuCl$_2$(CH$_3$CN)$_4$+2C$_6$H$_8$===>2NEt$_3$===>
Ru(C$_6$H$_6$)(C$_6$H$_8$)+2Cl$^-$(HNEt$_3$)$^+$+4CH$_3$CN

Ru(II)Cl$_2$(acetonitrile)$_4$ (from Umicore, Hanau, 29.3% by weight of Ru, 10 g, 29 mmol) and NEt$_3$ (12.3 ml, 90 mol, 3 eq.) are initially charged in a flask. Ethanol (100 ml), demineralized water (50 ml) and 1,4-cyclohexadiene (from Aldrich, 11.4 ml, 116 mmol, 4 eq.) are added. The reaction mixture is inertized with protective gas and brought to reflux (oil bath temperature 90° C.). The resulting red-brown solution is stirred at reflux for 3 hours and then cooled to room temperature. 100 ml of demineralized water are added. The reaction mixture is filtered through a D4 glass frit. The filtercake is washed with water. The resulting product in the form of yellow needles is dried to constant weight under vacuum at room temperature.

Yield: 6.35 g, 85%.

EXAMPLE 6

Preparation of ($\eta^6$-benzene)($\eta^4$-1,3-cyclohexadiene)ruthenium(0) from 1,4-cyclohexadiene in Ethanol/Water (One-Pot Process)

Reaction Equations:
Stage 1:

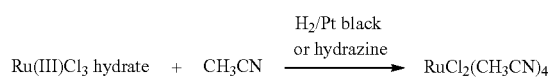

Ru(III)Cl$_3$ hydrate + CH$_3$CN $\xrightarrow{\text{H}_2/\text{Pt black or hydrazine}}$ RuCl$_2$(CH$_3$CN)$_4$ Stage 2:

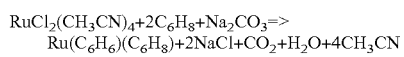

RuCl$_2$(CH$_3$CN)$_4$+2C$_6$H$_8$+Na$_2$CO$_3$=>
Ru(C$_6$H$_6$)(C$_6$H$_8$)+2NaCl+CO$_2$+H$_2$O+4CH$_3$CN

In Stage 1, Ru(III)Cl$_3$ hydrate (from Umicore Hanau, 40.1% by weight of Ru, 60 g, 0.24 mol) or Ru(III) chloride solution (from Umicore Hanau, 20% by weight of Ru, 121 g, 0.24 mol) are initially charged in a flask, and dissolved in EtOH (500 ml), and acetonitrile (70 ml). The brown-orange suspension is admixed at reflux with a reducing agent (hydrogen/Pt black or hydrazine); Ru(III)Cl$_3$ is thus reduced to Ru(II) and converted to Ru(II)Cl$_2$(CH$_3$CN)$_4$.

In Stage 2, demineralized water (200 ml), Na$_2$CO$_3$ (76 g, 0.71 mol, 3 eq.) and 1,4-cyclohexadiene (from Aldrich, 78 ml, 0.83 mol, 3.5 eq.) are added to the resulting yellow-orange suspension. The mixture is stirred at reflux for 3 hours. Then 300 ml of solvent mixture are distilled off. The product is extracted with hexane or toluene, and the organic phase is washed with demineralized water, dried over MgSO$_4$ and activated carbon, filtered and then concentrated to dryness. The resulting product in the form of yellow needles is dried to constant weight under reduced pressure at room temperature.

Yield: 40 g, 65%. Purity: ≥98% ($^1$H NMR).

EXAMPLE 7

Preparation of ($\eta^6$-benzene)($\eta^4$-1,3-cyclohexadiene)ruthenium(0) from 1,4-cyclohexadiene and RuCl$_2$(DMSO)$_4$ in Ethanol/Water Reaction Equation:

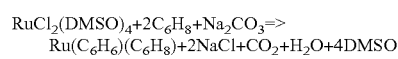

RuCl$_2$(DMSO)$_4$+2C$_6$H$_8$+Na$_2$CO$_3$=>
Ru(C$_6$H$_6$)(C$_6$H$_8$)+2NaCl+CO$_2$+H$_2$O+4DMSO

Ru(II)Cl$_2$(Dimethyl sulphoxide)$_4$ (from Umicore Hanau, 20.8% by weight of Ru, 5 g, 10 mmol) and Na$_2$CO$_3$ (4.3 g, 40 mmol, 4 eq.) are initially charged in a flask. Ethanol (50 ml), demineralized water (25 ml) and 1,4-cyclohexadiene (from Aldrich, 4 ml, 40 mmol, 4 eq.) are added. The suspension is inertized with protective gas and brought to reflux (oil bath temperature 90° C.). The brown mixture is stirred at reflux for 3 hours and then cooled to room temperature. 100 ml of demineralized water are added. The reaction mixture is filtered through a D4 glass frit. The filtercake is washed with water. The resulting product in the form of yellow needles is dried to constant weight under reduced pressure at room temperature.

Yield: 1.9 g, 72%; Purity: ≥98% ($^1$H NMR).

EXAMPLE 8

Preparation of ($\eta^6$-benzene)($\eta^4$-1,5-cyclooctadiene)ruthenium(0) from 1,4-cyclohexadiene and 1,5-cyclooctadiene in Ethanol/Water Structural Formula:

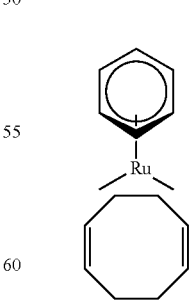

Reaction Equation:

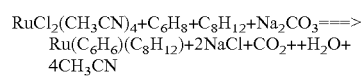

RuCl$_2$(CH$_3$CN)$_4$+C$_6$H$_8$+C$_8$H$_{12}$+Na$_2$CO$_3$===>
Ru(C$_6$H$_6$)(C$_8$H$_{12}$)+2NaCl+CO$_2$++H$_2$O+
4CH$_3$CN

Ru(II)Cl$_2$(acetonitrile)$_4$ (from Umicore Hanau, 29.3% by weight of Ru, 10 g, 29 mmol) and Na$_2$CO$_3$ (12.3 g, 120 mmol, 4 eq.) are initially charged in a flask. Ethanol (100 ml), water (50 ml), 1,4-cyclohexadiene (2.9 ml, 29 mmol, 1 eq.) and 1,5-cyclooctadiene (10.8 ml, 87 mmol, 3 eq.) are added. The suspension is inertized with protective gas and brought to reflux (oil bath temperature 90° C.). The pale brown-orange mixture is stirred at reflux for 4 hours and then cooled to room temperature. The reaction mixture is extracted with n-hexane. The organic phase is washed once with water and dried over MgSO$_4$ and activated carbon, then filtered. The clear yellow solution is subjected to rotary evaporation, and the resulting crystalline pale yellow product is washed with ethanol and then dried to constant weight under reduced pressure at room temperature.

Yield: 5 g, 60%; Purity: ≥98% ($^1$H NMR).

$^1$H NMR (CD$_2$Cl$_2$), δ(ppm): 1.8-2.2 (m, 12H, CH$_2$), 3.35 (m, 4H, CH, 1,5-cyclooctadiene), 5.25 (m, 6H, CH, benzene).

EXAMPLE 9

Preparation of (η$^6$-p-cymene)(η$^4$-1-isopropyl-4-methylcyclohexadiene)ruthenium(0) as an Isomer Mixture from α-terpinene Structural Formulae:

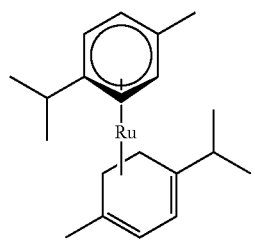

Isomer A

Isopropyl-4-methyl-1,3-cyclohexadiene

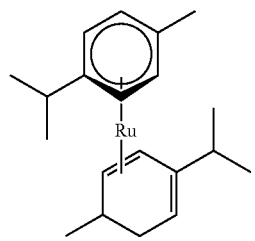

Isomer B

1-Isopropyl-4-methyl-1,5-cyclohexadiene

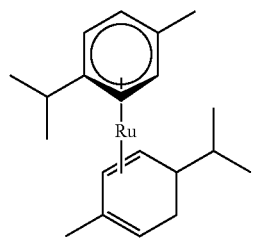

Isomer C

1-Isopropyl-4-methyl-3,5-cyclohexadiene

Reaction Equation:

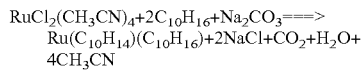

Ru(II)Cl$_2$(acetonitrile)$_4$ (from Umicore Hanau, 29.3% by weight of Ru, 10 g, 29 mmol) and Na$_2$CO$_3$ (12.4 g, 120 mmol, 4 eq.) are initially charged in a flask. Ethanol (100 ml), demineralized water (50 ml) and 1-isopropyl-4-methyl-1,3-cyclohexadiene (α-terpinene, from Aldrich, 17.4 ml, 102 mmol, 3.5 eq.) are added. The suspension is inertized with protective gas and brought to reflux (oil bath temperature 85° C.). The pale brown-orange mixture is stirred at reflux for three hours and then cooled to room temperature. The product is extracted with hexane or toluene. The organic phase is washed with water, dried over MgSO$_4$, filtered and then concentrated to dryness. The resulting yellow-orange oil is dried to constant weight under high vacuum at 90° C. As evident from the $^{13}$C NMR spectrum and the $^1$H NMR spectrum, the product consists of a mixture of the three isomers A, B and C. Yield: 9.1 g, 85%. Purity: ≥90% (1H NMR).

The analysis of the $^1$H NMR spectrum confirms the presence of an isomer mixture. In the $^1$H spectrum there are seven signals in the range of δ=4.5 to 5.2 ppm, which can be assigned to the protons of the olefinic carbons of the diene or arene; their integral ratio of 2.8:1:0.8:0.8:1.6:1:1 shows that an isomer mixture is present.

For isomer A, four signals would be expected within this range (two from the arene and two from the diene in a ratio of 2:2:1:1). For isomers B and C, three signals each would be expected in this range (two from the arene and one from the diene in a ratio of 2:2:1). The signals of the olefinic protons on carbons C2 and C5 (in isomer B) and on carbons C3 and C6 (in isomer C) are in the range of δ=2.6 to 2.9 ppm. An exact assignment is impossible since many signals are superimposed; however, the evaluation of the intensities shows that at least two of the isomers are present in a ratio of about 1:0.8 (i.e. 1.25:1).

$^1$H NMR (benzene-d$_6$): δ=5.01-5.07 (m), 4.97 (d, J=5.7 Hz), 4.88 (d, J=5.7 Hz), 4.86 (d, J=5.4 Hz), 4.72-4.77 (m), 4.68 (d, J=5.4 Hz), 4.58 (d, J=5.7 Hz), 2.77-2.84 (m), 2.67 (m), 2.35 (dq), 2.05-2.24 (m), 1.93 (s), 1.89-1.99 (m), 1.86-1.88 (m), 1.84 (s), 1.44-1.55 (m), 1.31 (ddd, J=13.0, 4.0, 1.9 Hz), 1.20 (dd, J=6.9, 2.5 Hz), 1.07-1.17 (m), 1.02 (d, J=6.9 Hz), 0.96 ppm (d, J=6.6 Hz).

$^{13}$C NMR (benzene-d$_6$): δ=105.5 (C), 105.2 (C), 103.0 (C), 93.4 (C), 93.2 (C), 90.1 (C), 81.9 (CH), 81.7 (CH), 81.5 (CH), 81.2 (CH), 79.7 (CH), 79.6 (CH), 79.5 (CH), 79.3 (CH), 77.4 (CH), 72.6 (CH), 60.8 (CH), 55.4 (CH), 53.0 (CH), 49.5 (CH), 38.9 (CH), 38.5 (CH$_2$), 34.3 (CH), 33.2 (CH), 33.1 (CH$_2$), 26.0 (CH$_3$), 24.8 (CH$_3$), 24.6 (CH$_3$), 24.4 (CH$_3$), 24.4 (CH$_3$), 24.2 (CH$_3$), 22.9 (CH$_3$), 21.7 (CH$_3$), 21.6 (CH$_3$), 20.5 (CH$_3$), 20.2 (CH$_3$) ppm.

Mass spectrum (MS): The most intense ion, [M-H]$^+$, is at m/z=371.1309 and corresponds to the monoisotopic empirical formula C$_{20}$H$_{29}^{102}$Ru with a deviation of 0.37 ppm.

EXAMPLE 10

Preparation of (η$^6$-p-cymene)(η$^4$-1-isopropyl-4-methylcyclohexadiene)ruthenium(0) as an Isomer Mixture from γ-terpinene with NEt$_3$ as a Base Structural Formula: See Example 9

Reaction Equation:

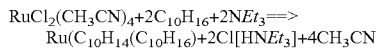

Ru(II)Cl$_2$(acetonitrile)$_4$ (from Umicore Hanau, 29.3% by weight of Ru, 10 g, 29 mmol) is initially charged in a flask. Acetone (150 ml), water (60 ml), NEt$_3$ (12.3 ml, 90 mmol, 3 eq.) and 1-isopropyl-4-methyl-1,4-cyclohexadiene (γ-terpinene, from Aldrich, 11 ml, 67 mmol, 2.3 eq.) are added. The suspension is inertized with protective gas and brought to reflux (oil bath temperature 75° C.). The brown-orange mixture is stirred at reflux for three hours and then cooled to room temperature. The product is extracted with hexane or toluene. The organic phase is washed with water, dried over MgSO$_4$ and activated carbon, filtered and then concentrated to dryness. The resulting yellow-orange oil is dried to constant weight under high vacuum at 90° C. The product is characterized by means of $^{13}$C NMR and $^1$H NMR spectra, and corresponds to the product from Example 9.

Yield: 9.7 g, 90%; Purity: ≥90% ($^1$H NMR).

EXAMPLE 11

Preparation of ($\eta^6$-p-cymene)($\eta^4$-1-isopropyl-4-methylcyclohexadiene)ruthenium(0) as an Isomer Mixture from α-phellandrene Structural Formula: See Example 9
Reaction Equation: See Example 9
Ru(II)Cl$_2$(acetonitrile)$_4$ (from Umicore Hanau, 29.3% by weight of Ru, 10 g, 29 mmol) and Na$_2$CO$_3$ (12.4 g, 120 mmol, 4 eq.) are initially charged in a flask. Ethanol (100 ml), water (50 ml) and 2-methyl-5-isopropyl-1,3-cyclohexadiene (α-phellandrene, from Aldrich, 9.6 ml, 58 mmol, 2 eq.) are added. The suspension is inertized with protective gas and brought to reflux (oil bath temperature 85° C.). The pale brown-orange mixture is stirred at reflux for three hours and then cooled to room temperature. The product is extracted with hexane or toluene. The organic phase is washed with water, dried over MgSO$_4$, filtered and then concentrated to dryness. The resulting yellow-orange oil is dried to constant weight under high vacuum at 90° C. The product is characterized by means of NMR spectra and corresponds to the product from Examples 9 and 10.

Yield: 8.6 g, 80%; Purity: ≥90% ($^1$H NMR).

What is claimed is:
1. Process for preparing ruthenium(0)-olefin complexes of the (arene)(diene)Ru(0) type by reacting a ruthenium starting compound of the formula

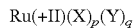

in which
X=an anionic group,
Y=an uncharged two-electron donor ligand,
p=1 or 2,
q=an integer from 1 to 6,
with a cyclohexadiene derivative or a diene mixture comprising a cyclohexadiene derivative, in the presence of a base, wherein the arene bound in the ruthenium(0)-olefin complex is formed from this cyclohexadiene derivative by oxidation.

2. Process according to claim 1, wherein the cyclohexadiene derivative is an unsubstituted cyclohexadiene derivative selected from the group consisting of 1,3-cyclohexadiene, 1,4-cyclohexadiene, and mixtures thereof.

3. Process according to claim 1, wherein the cyclohexadiene derivative is a mono- or poly-alkyl-substituted cyclohexadiene and is selected from the group consisting of 1-methyl-1,3-cyclohexadiene, 1-methyl-1,4-cyclohexadiene, 1-ethyl-1,3-cyclohexadiene, 1-ethyl-1,4-cyclohexadiene, 1-isopropyl-4-methyl-1,3-cyclohexadiene (α-terpinene), 1-isopropyl-4-methyl-1,4-cyclohexadiene (γ-terpinene), 2-methyl-5-isopropyl-1,3-cyclohexadiene (α-phellandrene), bicyclo-[4.3.0]-nona-3,6(1)-diene, and mixtures thereof.

4. Process according to claim 1, wherein the diene mixture comprises, in addition to the cyclohexadiene derivative, a substituted or unsubstituted cyclic diene selected from the group consisting of 1,3-cyclooctadiene, 1,5-cyclooctadiene, norbornadiene, dicyclopentadiene, spiro[2.4]hepta-4,6-diene and mixtures thereof.

5. Process according to claim 1, wherein the diene mixture comprises, in addition to the cyclohexadiene derivative, a substituted or unsubstituted noncyclic diene selected from the group consisting of butadiene, isoprene, 2,3-dimethyl-1,3-butadiene, 1,3-pentadiene, 1,4-pentadiene, 2,4-dimethyl-1,3-pentadiene and mixtures thereof.

6. Process according to claim 1, wherein the diene mixture comprises diene analogs such as 1,3-divinyltetramethyldisiloxane (VTS) or 1,3-divinyltetramethyldisilazane.

7. Process according to claim 1, wherein the amount of the cyclohexadiene derivative or of the diene mixture added is 2 to 5 equivalents (based on the Ru starting compound).

8. Process according to claim 1, wherein the uncharged two-electron donor ligand Y is selected from the group consisting of acetonitrile, benzonitrile, acrylonitrile, methylisonitrile (CNCH$_3$), water, THF, dioxane, dimethyl sulphoxide (DMSO), dimethylformamide (DMF), acetone, ammonia (NH$_3$), amines, pyridine, and mixtures and combinations thereof.

9. Process according to claim 1, wherein the uncharged two-electron donor ligand Y is a solvent ligand and is selected from the group consisting of acetonitrile, benzonitrile, water, THF, dioxane, dimethyl sulphoxide (DMSO), dimethylformamide (DMF), acetone, pyridine, and mixtures and combinations thereof.

10. Process according to claim 1, wherein the anionic X group of the ruthenium(II) starting compound comprises halides, pseudohalides, acetylacetonates, tosylates (CH$_3$C$_6$H$_4$SO$_3^-$), trifluoromethylsulphonates ("triflate"; CF$_3$SO$_3^-$), acetates, trifluoroacetates, sulphates (SO$_4^{2-}$), hydrogenphosphates (HPO$_4^{2-}$), oxalates (C$_2$O$_4^{2-}$) or carbonates (CO$_3^{2-}$).

11. Process according to claim 1, wherein the ruthenium (II) starting compound is RuCl$_2$(acetonitrile)$_4$, RuBr$_2$(acetonitrile)$_4$, RuCl$_2$(pyridine)$_4$, [Ru(H$_2$O)$_6$]Cl$_2$, [Ru(H$_2$O)$_6$](triflate)$_2$, RuCl$_2$(DMSO)$_4$, [Ru(NH$_3$)$_6$]Cl$_2$ or RuCl$_2$(benzonitrile)$_4$ or a mixture thereof.

12. Process according to claim 1, wherein the base used comprises inorganic bases such as alkali metal hydroxides, alkaline earth metal hydroxides, basic oxides, alkali metal carbonates, alkaline earth metal carbonates, alkali metal hydrogencarbonates, alkaline earth metal hydrogencarbonates, alkali metal oxalates, alkaline earth metal oxalates, alkali metal acetates, alkaline earth metal acetates, alkali metal phosphates, alkaline earth metal phosphates or mixtures thereof.

13. Process according to claim 1, wherein the base used comprises organic bases such as diethylamine, trimethylamine, triethylamine, urotropin, ethanolamine, imidazole, pyridine, ethylenediamine or mixtures thereof.

14. Process according to claim 1, wherein the amount of the base is 1 to 10 equivalents (based on the ruthenium compound).

15. Process according to claim 1, wherein the process is performed in a polar organic solvent, a mixture of polar organic solvents or a mixture of a polar organic solvent with water.

16. Process according to claim 1, wherein the Ru(II) starting compound of the formula Ru(+II)(X)$_p$(Y)$_q$ is prepared in a preceding step and used without intermediate isolation.

17. Process according to claim 16, wherein the Ru(II) starting compound is Ru(II)Cl$_2$(CH$_3$CN)$_4$ or Ru(II)Cl$_2$(DMSO)$_4$ and is prepared by reduction of ruthenium(III) chloride hydrate.

18. A method for preparing homogeneous catalysts comprising using the Ru(0)-olefin complexes prepared by the process according to claim 1.

19. A method for preparing functional ruthenium- or ruthenium oxide-containing coatings comprising using the Ru(0)-olefin complexes prepared by the process according to claim 1.

20. Isomer mixture of the compound ($\eta^6$-p-cymene)($\eta^4$-1-isopropyl-4-methyl-cyclohexadiene)ruthenium(0) comprising at least two of the three isomers ($\eta^6$-p-cymene)($\eta^4$-1-isopropyl-4-methyl-1,3-cyclohexadiene)ruthenium(0), ($\eta^6$-p-cymene)($\eta^4$-1-isopropyl-4-methyl-1,5-cyclohexadiene)ruthenium(0) and ($\eta^6$-p-cymene)($\eta^4$-1-isopropyl-4-methyl-3,5-cyclohexadiene)ruthenium(0).

21. Isomer mixture according to claim 20, wherein at least two of the isomers are present in a ratio of 1:5 to 5:1.

22. A method for producing ruthenium-containing layers by means of thin film technology which comprises using the isomer mixture according to claim 20.

23. Process according to claim 7, wherein the amount of the cyclohexadiene derivative or of the diene mixture added is 2 to 4 equivalents (based on the Ru starting compound).

24. Process according to claim 14, wherein the amount of the base is 2 to 5 equivalents (based on the ruthenium compound).

* * * * *